US00PP22514P2

(12) United States Plant Patent
Smith

(10) Patent No.: US PP22,514 P2
(45) Date of Patent: Feb. 21, 2012

(54) ***CHRYSANTHEMUM* PLANT NAMED 'SYNGIGI YEL'**

(50) Latin Name: *Chrysanthemum×morifolium*
Varietal Denomination: Syngigi Yel

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/925,038

(22) Filed: Oct. 12, 2010

(51) Int. Cl.
*A01H 5/00* (2006.01)

(52) U.S. Cl. ..... Plt./289

(58) Field of Classification Search ..... Plt./289
See application file for complete search history.

*Primary Examiner* — Susan McCormick Ewoldt
(74) *Attorney, Agent, or Firm* — S. Matthew Edwards

(57) ABSTRACT

A new *Chrysanthemum* plant named 'Syngigi Yel' particularly distinguished by the small, bold yellow flowers; strong and stiff peduncles, medium green foliage, and compact and mounded plant habit.

1 Drawing Sheet

Latin name of the genus and species of the plant claimed: *Chrysanthemum×morifolium.*

Varietal denomination: 'Syngigi Yel'.

BACKGROUND OF THE NEW PLANT

The present invention comprises a new *Chrysanthemum,* botanically known as *Chrysanthemum×morifolium,* and hereinafter referred to by the variety name 'Syngigi Yel'.

'Syngigi Yel' is a product of a planned breeding program. The new cultivar has small, bold yellow flowers, strong and stiff peduncles, medium green foliage, and compact and mounded plant habit.

'Syngigi Yel' originates as a natural whole plant mutation of 'Yogigi Snow', U.S. Pat. No. 21,783, and was discovered and selected by the inventor as a single flowering plant within a population of the parent cultivar in a controlled breeding program in Alva, Fla., in November 2004. The parent cultivar 'Yogigi Snow' has white flowers.

The first act of asexual reproduction of 'Syngigi Yel' was accomplished when vegetative cuttings were propagated from the initial selection in December 2004 in a controlled environment in Alva, Fla.

BRIEF SUMMARY OF INVENTION

Horticultural examination of plants grown from cuttings of the plant initiated in December 2004, and continuing thereafter, has demonstrated that the combination of characteristics as herein disclosed for 'Syngigi Yel' are firmly fixed and are retained through successive generations of asexual reproduction.

'Syngigi Yel' has not been observed under all possible environmental conditions. The phenotype may vary significantly with variations in environment such as temperature, light intensity and day length.

Plant Breeder's Rights for this cultivar were applied for in Canada on Oct. 30, 2009 (09-6793) and in CVPO on Jan. 29, 2010 (2010/0195). 'Syngigi Yel' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'Syngigi Yel' with colors being as true as possible with an illustration of this type. The photographic drawing shows a flowering potted plant of the new variety, and a close-up of the flowers.

DETAILED BOTANICAL DESCRIPTION

The plant descriptions, measurements and aforementioned photographs were taken in Gilroy, Calif. in May under natural light. These plants were grown in a greenhouse under conditions which approximate those generally used in commercial potted *Chrysanthemum* production in Gilroy, Calif. These plants used in the photograph and descriptions were about 12-14 weeks of age.

Color references are made to The Royal Horticultural Society Colour Chart (R.H.S.) 2001.

TABLE 1

DIFFERENCES BETWEEN THE NEW VARIETY 'SYNGIGI YEL' AND A SIMILAR VARIETY: 'JANICE' (U.S. Plant Pat. No. 9,817)

| | 'Syngigi Yel' | 'Janice' (U.S. Plant Pat. No. 9,817) |
|---|---|---|
| Flower color: | More yellow/less gold | More gold |
| Flower size: | Smaller | Larger |
| Plant habit: | Rounded and more compact | Less round/compact |

Plant:

*Form, growth and habit.*—Herbaceous decorative garden-type. Stems upright and outwardly spreading on short, mounded and compact plants, with strong and stiff branches.

*Plant height.*—About 10 cm.

*Plant height* (*inflorescence included*).—12-14 cm.
*Plant width.*—25 cm.
*Garden performance and tolerance to weather.*—Very good.
*Crop time to flowering.*—About 10 weeks.

Roots:
*Number of days to initiate roots.*—4 days at about 22 degrees C.
*Number of days to produce a rooted cutting.*—7-10 days at 22 degrees C.
*Type.*—Fine, fibrous, free branching.
*Color.*—RHS N155B but whiter.

Foliage:
*Arrangement.*—Alternate.
*Immature, leaf color, upper surface.*—RHS 137A but a little darker.
*Lower surface.*—Closest to RHS N138B.
*Mature, leaf color, upper surface.*—RHS 137A but a little darker.
*Lower surface.*—Closest to RHS N138B.
*Length.*—4.0-4.5 cm.
*Width.*—2.9-3.5 cm.
*Shape.*—Ovate.
*Base shape.*—Attenuate.
*Apex shape.*—Mucronulate.
*Margin.*—Serrate.
*Texture, upper surface.*—Bifid T-shaped hairs.
*Lower surface.*—Bifid T-shaped hairs.
*Color of veins, upper surface.*—RHS 146D.
*Color of veins, lower surface.*—RHS 146D.
*Petiole color.*—RHS 146D.
*Length.*—0.9-1.1 cm.
*Diameter.*—0.1 cm.
*Texture.*—Bifid T-shaped hairs.

Stem:
*Quantity of main branches per plant.*—6-7.
*Color of stem.*—Closest to RHS 146D.
*Length of stem.*—9-11 cm.
*Diameter.*—0.3-0.4 cm.
*Length of internodes.*—0.4-0.7 cm.
*Texture.*—Bifid T-shaped hairs.
*Color of peduncle.*—RHS 144A.
*Length of peduncle.*—4-5 cm.
*Peduncle diameter.*—0.1 cm.
*Texture.*—Bifid T-shaped hairs.

Inflorescence:
*Type.*—Compositae type, solitary inflorescences (decorative-type) borne terminally above foliage, ray florets arranged acropetally on a capitulum.
*Natural flowering season.*—About mid-September.
*Quantity of inflorescences per plant.*—46-50 and numerous buds.
*Lastingness of individual blooms on the plant.*—About 4 weeks.
*Fragrance.*—Slightly spicy.

BUD (just when opening/showing color):
*Color.*—RHS 4B with a RHS 6A apex.
*Length.*—0.7-0.9 cm.
*Width* (*cm*).—0.9-1.0 cm.
*Shape.*—Oblate.

Immature inflorescence:
*Diameter.*—3.0-3.2 cm.
*Color of ray florets, upper surface.*—RHS 6A.
*Lower surface.*—RHS 6C.

Mature inflorescence:
*Diameter.*—4.0-4.2 cm.
*Depth.*—1.5 cm.
*Total diameter of 'disc'.*—0.5-0.7 cm.
*Receptacle height.*—0.2 cm.
*Receptacle diameter.*—0.5 cm.

Ray florets:
*Average quantity of florets.*—About 135 in numerous whorls.
*Color of florets, upper surface.*—RHS 6B maturing to about RHS 9A to RHS 9B.
*Lower surface.*—RHS 8B.
*Length.*—1.7-2.1 cm.
*Width.*—0.6-0.7 cm.
*Shape.*—Obovate.
*Apex shape.*—Irregularly emarginated to praemorse.
*Margin.*—Entire.
*Texture, upper surface.*—Papillose.
*Lower surface.*—Papillose.

Disc florets:
*Average quantity of florets.*—About 50.
*Color of florets.*—Close to RHS 144D with a RHS 13A apex.
*Length.*—0.4-0.5 cm.
*Width.*—0.1 cm.
*Shape.*—Tubular, elongated.
*Apex shape.*—Acute, 5 pointed.

Phyllaries:
*Quantity.*—About 20.
*Color, upper surface.*—RHS 137C.
*Lower surface.*—RHS 137C.
*Length.*—0.4-06. cm.
*Width.*—0.1-0.15 cm.
*Shape.*—Lanceolate.
*Apex shape.*—Acute.
*Based.*—Fused.
*Margins.*—Entire; with papery edges.
*Texture, upper surface.*—Smooth, glabrous.
*Lower surface.*—Bifid T-shaped hairs.

Reproductive organs:
*Found on both floret types.*—
*Pistil.*—1.
*Length.*—0.4-0.5 cm.
*Style color.*—RHS 1C with a little more green.
*Style length.*—0.3-0.4 cm.
*Stigma color.*—RHS 3A.
*Stigma shape.*—Bi-parted.
*Ovary color.*—Not observed.
*Found on only disc florets.*—
*Stamens.*—1.
*Color of filaments.*—RHS 155C.
*Length filaments.*—0.1-0.2 cm.
*Anther color.*—RHS 13B.
*Anther length.*—0.1 cm.
*Anther shape.*—Ovate.
*Color of pollen.*—RHS 15B.
*Pollen amount.*—About average.
*Fertility/seed set.*—Has not been observed on this hybrid.

Disease/pest resistance: Disease/pest resistance has not been observed on this hybrid.

What is claimed is:

1. A new and distinct variety of *Chrysanthemum* plant named 'Syngigi Yel' substantially as illustrated and described herein.

* * * * *

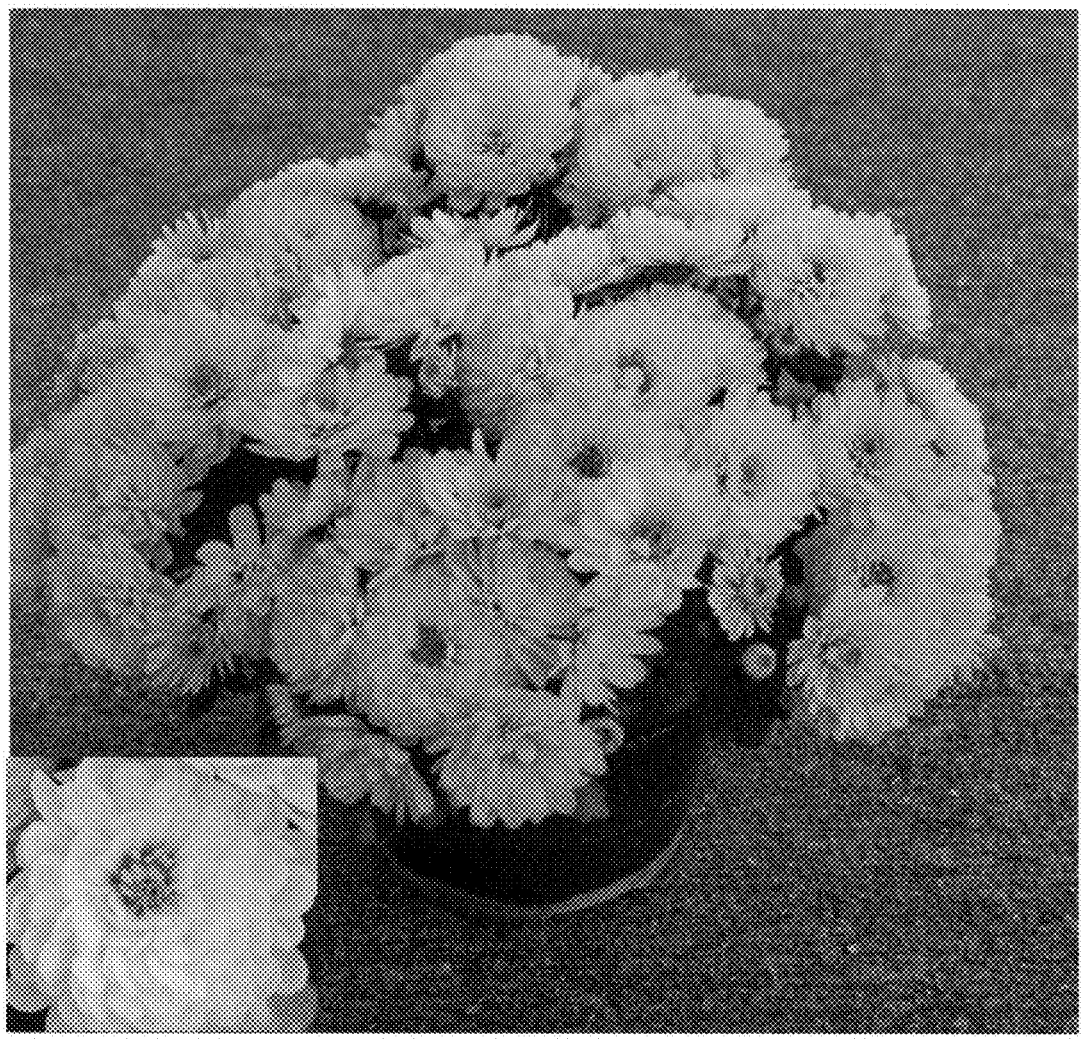

UNITED STATES PATENT AND TRADEMARK OFFICE

CERTIFICATE OF CORRECTION

PATENT NO. : PP22,514 P2
APPLICATION NO. : 12/925038
DATED : February 21, 2012
INVENTOR(S) : Smith It is certified that error appears in the above-identified patent and that said Letters Patent is hereby corrected as shown below:

At column 4, line 28, please delete "06." and insert therefor --0.6--

Signed and Sealed this
Third Day of April, 2012

David J. Kappos

David J. Kappos
*Director of the United States Patent and Trademark Office*